(12) United States Patent
Blanck (10) Patent No.: US 9,186,270 B2
(45) Date of Patent: Nov. 17, 2015

(54) DYNAMIC EXOSKELETAL ORTHOSIS

(75) Inventor: Ryan Vaughn Blanck, Schertz, TX (US)

(73) Assignee: The United States of America as represented by The Secretary of the Army, Washington, DC (US)

( * ) Notice: Subject to any disclaimer, the term of this patent is extended or adjusted under 35 U.S.C. 154(b) by 80 days.

(21) Appl. No.: 13/450,539

(22) Filed: Apr. 19, 2012

(65) Prior Publication Data

US 2012/0271214 A1 Oct. 25, 2012

Related U.S. Application Data

(60) Provisional application No. 61/518,801, filed on Apr. 20, 2011.

(51) Int. Cl.
*A61F 5/01* (2006.01)

(52) U.S. Cl.
CPC .................................. *A61F 5/0111* (2013.01)

(58) Field of Classification Search
CPC ....... A61F 5/01; A61F 5/0102; A61F 5/0104; A61F 5/0111; A61F 5/0127
USPC .............. 602/5, 23, 26, 27, 12; 128/869, 882; 623/27–56; 2/22–24
See application file for complete search history.

(56) References Cited

U.S. PATENT DOCUMENTS

| | | | |
|---|---|---|---|
| 1,769,681 A * | 7/1930 | Ettinger ........................... | 602/23 |
| 2,796,866 A | 6/1957 | R. Cohen | |
| RE30,501 E * | 2/1981 | Almeida ......................... | 602/16 |
| 4,991,571 A | 2/1991 | Kausek | |
| 5,088,479 A * | 2/1992 | Detoro ............................. | 602/27 |
| 5,344,390 A * | 9/1994 | Motloch ......................... | 602/23 |
| 5,529,576 A | 6/1996 | Lundt et al. | |
| 5,981,112 A | 11/1999 | Roberts | |
| 6,007,506 A | 12/1999 | Heil | |
| 6,010,474 A | 1/2000 | Wycoki | |
| RE37,209 E | 6/2001 | Hensley et al. | |
| 6,537,238 B1 * | 3/2003 | Chignon ......................... | 602/23 |
| 6,793,638 B1 * | 9/2004 | DeToro et al. .................. | 602/23 |
| 6,827,696 B1 * | 12/2004 | Maguire ......................... | 602/27 |
| 6,945,946 B2 * | 9/2005 | Rooney .......................... | 602/27 |
| 7,112,180 B2 * | 9/2006 | Guenther ........................ | 602/23 |
| 7,270,644 B2 * | 9/2007 | Ingimundarson ............... | 602/27 |
| 7,462,160 B2 * | 12/2008 | Nobbe et al. .................... | 602/27 |
| 7,513,880 B2 * | 4/2009 | Ingimundarson et al. ...... | 602/23 |
| 7,727,173 B2 * | 6/2010 | Rooney .......................... | 602/23 |
| 7,819,832 B2 | 10/2010 | Balzer | |
| 8,425,440 B2 * | 4/2013 | DeToro et al. .................. | 602/16 |
| 8,465,445 B2 * | 6/2013 | George .......................... | 602/23 |
| 8,480,604 B2 * | 7/2013 | Messer ............................ | 602/6 |
| 2005/0137510 A1 | 6/2005 | Dauny | |
| 2006/0079822 A1 * | 4/2006 | Hjorth ............................ | 602/28 |

(Continued)

OTHER PUBLICATIONS

Galvan, S., et al., "Orthopedic Device Helping Wounded Warriors Return to Run," Aug. 12, 2011.

(Continued)

*Primary Examiner* — Alireza Nia
*Assistant Examiner* — Raymond E Harris
(74) *Attorney, Agent, or Firm* — Cahn & Samuels, LLP (57) ABSTRACT

An exoskeletal orthosis includes a proximal cuff comprising a hinge along an upper edge of the cuff; an ankle section/footplate; and at least one posterior strut connecting the proximal cuff to the ankle section and foot plate.

18 Claims, 5 Drawing Sheets

(56) References Cited

U.S. PATENT DOCUMENTS

| | | | | |
|---|---|---|---|---|
| 2006/0270958 | A1* | 11/2006 | George | 602/28 |
| 2006/0276736 | A1* | 12/2006 | Devreese | 602/27 |
| 2007/0027421 | A1 | 2/2007 | Nobbe et al. | |
| 2010/0030123 | A1* | 2/2010 | DeToro et al. | 602/28 |
| 2010/0056970 | A1 | 3/2010 | Nace | |
| 2010/0101118 | A1* | 4/2010 | Guenther | 36/140 |
| 2010/0204631 | A1* | 8/2010 | Rooney | 602/23 |
| 2012/0271214 | A1 | 10/2012 | Blanck | |
| 2013/0165833 | A1 | 6/2013 | Blanck | |

OTHER PUBLICATIONS

Marini, R., "GIs Bracing for New Action," http://www.express-news.net, Sep. 4, 2011.

Masulli, J., http://www.njherald.com/story/news/.

Owens, J., et al., Return to Running and Sports Participation After Limb Salvage, The Journal of Trauma Injury, Infection, and Critical Care, Jul. 2011, vol. 71, No. 1.

Patzkowski, J., et al., "Can an Ankle-Foot Orthosis Change Hearts and Minds?", Journal of Surgical Orthopaedic Advances, 2011, pp. 8-18, vol. 20, No. 1.

Rigby, W., "Up and Running: Device Readies Wounded Warriors for Action," Kens 5 San Antonio, Aug. 12, 2011.

Robbins, S., "Device Might Offer Some Troops an Alternative to Amputation," Stars and Stripes, Sep. 21, 2011.

Sanchez, E., New Brace Salvages Limbs, Mobility, Morale, Defense.gov, Dec. 8, 2011.

Tan, M., "Damaged Legs Made Fit," Army Times, Aug. 29, 2011.

Patzkowski, J., et al., "Comparative Effect of Orthosis Design on Functional Performance," The Journal of Bone and Joint Surgery, 2012, pp. 507-515, vol. 94.

Judd Lundt et al., "The USMC Strut Technology Applied to AFOs", American Academy of Orthotists and Prosthetists, Journal of Proceedings, 2000.

Judd Lundt et al., "The USMC LITTIG Dynamic Response Hip, Redesigned", American Academy of Orthotists and Prosthetists, Journal of Proceedings, 2000.

Future Design Fabrications: Custom Prosthetics and Orthotic Devices. http://www.futuredesignfabrications.com/orthotics.html, printed on Oct. 1, 2014.

* cited by examiner

DYNAMIC EXOSKELETAL ORTHOSIS

RELATED APPLICATION

This application claims priority to U.S. Provisional Patent Application Ser. No. 61/518,801 filed in the U.S. Patent and Trademark Office on Apr. 20, 2011, the entirety of which is incorporated herein by reference.

FIELD OF INVENTION

The present invention is directed to an ankle foot orthosis or brace, in particular to a dynamic exoskeletal orthosis.

BACKGROUND

Orthotics are devices that are made to correct or maintain alignment of different parts of the body, hence the name "braces."

An ankle foot orthosis (AFO) supports the joints of the foot, as well as the ankle. These devices can be used to protect, correct or limit motion at the joints by supporting a person's limb that has suffered from loss of strength or alignment due to disease or trauma. AFOs can be a solid design at the ankle with no motion allowed, or with joints to allow certain degrees of motion.

Historically, bracing options for those with pain/weakness/decreased range of motion about the ankle have been severely limited. The most common types of bracing either provided adequate strength compensation in the instance of an isolated peroneal neuropathy or were designed with very stiff orthotic materials that essentially immobilized the ankle and did not allow a more normal gait or higher level activities.

SUMMARY OF INVENTION

According to an aspect of the present invention, an exoskeletal orthosis comprises a proximal cuff comprising a hinge along an upper edge of the cuff; an ankle section/footplate; and at least one posterior strut connecting the proximal cuff to the ankle section/footplate.

According to another aspect of the present invention an orthosis comprises a proximal cuff comprising at least one hinge along an upper edge of the cuff; an ankle section/footplate; and at least one posterior strut attached at a proximal end to the proximal cuff and attached at a distal end to the ankle section/footplate. The ankle section/footplate comprises a suprarnalleolar ankle section having a lateral wing and a footplate section extending to the tips of a user's toes and having an arch.

According to another aspect of the invention, a method of treating an injury is provided comprising fitting an individual having an injury with an orthosis according to the present invention and placing the individual's foot with the attached orthosis inside a shoe or boot.

An advantage of the present invention is that the dynamic exoskeletal orthosis allows greater ability to walk and run despite severe lower extremity physical impairments.

Another advantage of the present invention is that the dynamic exoskeletal orthosis allows for early walking post-injury to high level activities with the same orthosis.

Yet another advantage of the present invention is that the dynamic exoskeletal orthosis may be lightweight, durable (tolerates impact of running with a ruck sack, for example, up to about 120 lbs.), and may be used in regular shoes and military boots.

As used herein "substantially", "relatively", "generally", "about", and "approximately" are relative modifiers intended to indicate permissible variation from the characteristic so modified. They are not intended to be limited to the absolute value or characteristic which it modifies but rather approaching or approximating such a physical or functional characteristic.

In this detailed description, references to "one embodiment", "an embodiment", or "in embodiments" mean that the feature being referred to is included in at least one embodiment of the invention. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

BRIEF DESCRIPTION OF THE DRAWINGS

FIG. 6b is a top view of the partial dynamic exoskeletal orthosis of FIG. 6a.

Given the following enabling description of the drawings, the methods and apparatus should become evident to a person of ordinary skill in the art.

DETAILED DESCRIPTION OF INVENTION

The orthosis of the present invention is designed to allow walking and running for individuals or patients with severe injury to the lower limb that causes reduced ankle range of motion, weakness, and pain. The orthosis allows for a range of activities including, but not limited to, early ambulation during the early post-injury phase, agility and impact activities, running, sprinting, and deploying with a military unit.

The orthosis of the present invention is designed to compensate for weakness, pain, and/or decreased range of motion (either alone or in combination) at the ankle that result from a variety of potential diagnoses including, but not limited to, ankle fusion, talus or calcaneus fractures, tibial nerve injuries, peroneal nerve injuries, partial foot amputation (which results in ankle plantarflexion weakness), soft tissue loss in the leg (resulting in inherent weakness), or pain in the ankle during weight bearing activities.

Current research suggests that the orthosis of the present invention not only compensates for weakness, but also generates forces about the ankle that more closely approaches the normal gait than other currently available orthoses. The article Patzowski et al., *Comparative Effect of Orthosis Design on Functional Performance*, J. Bone Joint Surg. Ab., 2012; 94:507-15, is incorporated by reference herein in its entirety. The article Patzowski et al., *Can an Ankle-Foot Orthosis Change Hearts and Minds?*", J. Surgical Orthopaedic Advances, 20(1):8-18, 2011, is also incorporated by reference herein in its entirety.

In specific embodiments, the orthosis of the present invention may be applied to the leg below the knee. The orthosis (also referred to as the Intrepid Dynamic Exoskeletal Orthosis or IDEO) may comprise the following components (description from the upper/proximal aspect to the lower/distal aspect).

A. Proximal Cuff

Figures 1, 2:
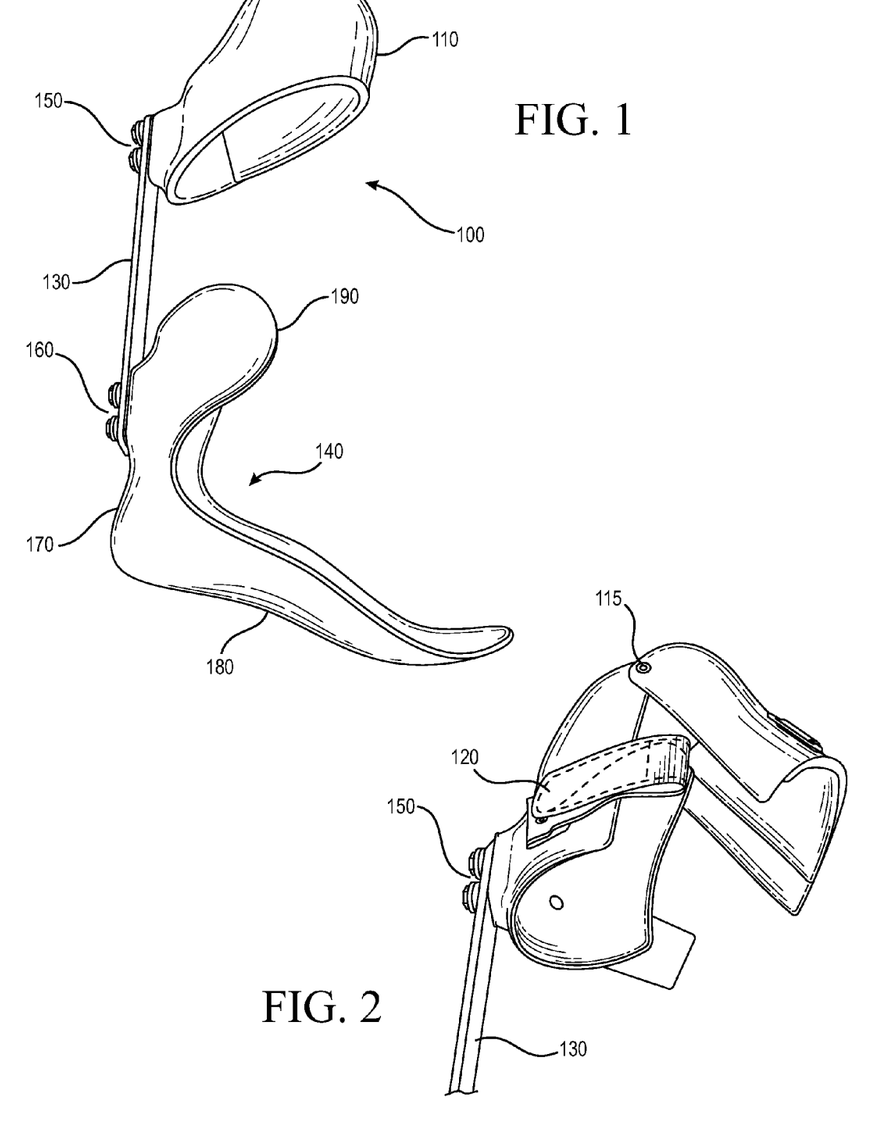
FIG. 1 is a side view of a dynamic exoskeletal orthosis according to an embodiment of the present invention.
FIG. 2 is a view of a proximal cuff of a dynamic exoskeletal orthosis according to an embodiment of the present invention.

With reference now to FIG. 1, the exoskeletal orthosis 100 according to the present invention comprises a proximal cuff 110. The proximal cuff may comprise at least one of a carbon material, reinforced carbon fiber composition, or resin material. The cuff may have a bivalve or a monolithic configuration.

A monolithic, one-piece, solid configuration comprises a solid cuff and is designed for a patient who has a stable size of the upper leg (calf and shin) and does not have limited ankle plantarflexion.

Figure 3:
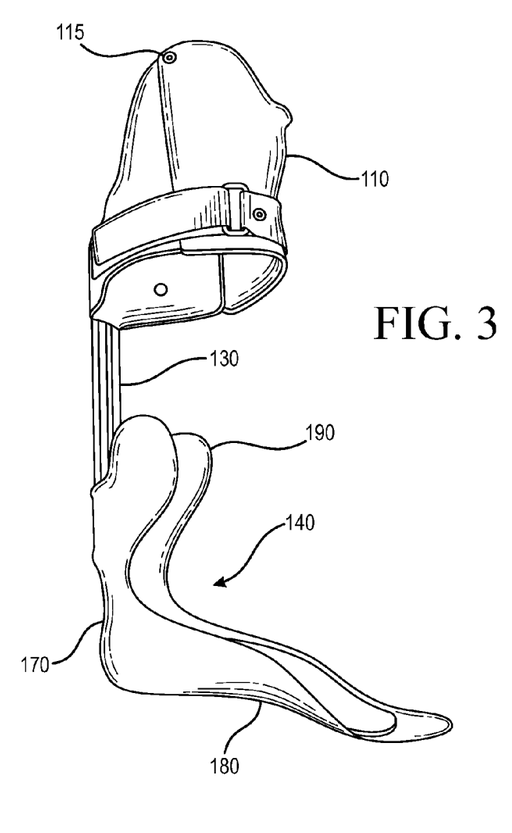
FIG. 3 is a view of a dynamic exoskeletal having a dual strut configuration according to another embodiment of the present invention.

A bivalve cuff comprises a hinge 115 (as shown in FIGS. 2-3) along an upper edge or aspect, thereby allowing the proximal cuff 110 to have a wider opening distally when donning the brace. This configuration may be utilized for patients who are not able to plantarflex the ankle enough to fit through a monolithic (solid) configuration and also allows for volume fluctuation of the upper leg. The hinge allows the proximal cuff to open upward due to a proximal fixed axis point.

In one or more embodiments, the proximal cuff 100 may have a strap 120 to help hold it in place while in use.

B. Posterior Strut

The exoskeletal orthosis 100 comprises at least one posterior strut 130 for connecting the proximal cuff 110 to an ankle/footplate section 140. The at least one posterior strut 130 may comprise a single bar or dual bars (as shown in FIG. 3), which may be bonded together. The at least one posterior strut may be of any shape for example, a flat bar, a cylindrical or tubular shape, or having a circular or semi-circular cross section. In one or more embodiments, the at least on posterior strut 130 may have a length of about 5 inches to about 12 inches.

In specific embodiments, the at least one posterior strut 130 may comprise an alignable dynamic carbon strut, for example, a TRULIFE Littig strut or a MEDI CLEVER BONE™ strut. The Littig strut was originally designed for use in the upper portion of hip disarticulation prostheses. The MEDI CLEVER BONE™ strut (bone system) may be designed for use as a dynamic pylon for transtibial prostheses.

The at least on posterior strut 130 may comprise at least one of a carbon material, reinforced carbon fiber composition, or resin material. In a specific embodiment, the at least one posterior strut may have an Aileron core.

In one or more embodiments, the at least on posterior strut may comprise an SLS material. Selective laser sintering (SLS) is an additive manufacturing technique that uses a high power laser (for example, a carbon dioxide laser) to fuse small particles of plastic, metal (direct metal laser sintering), ceramic, or glass powders into a mass that has a desired 3-dimensional shape.

C. Mounting Plates

Figure 4:
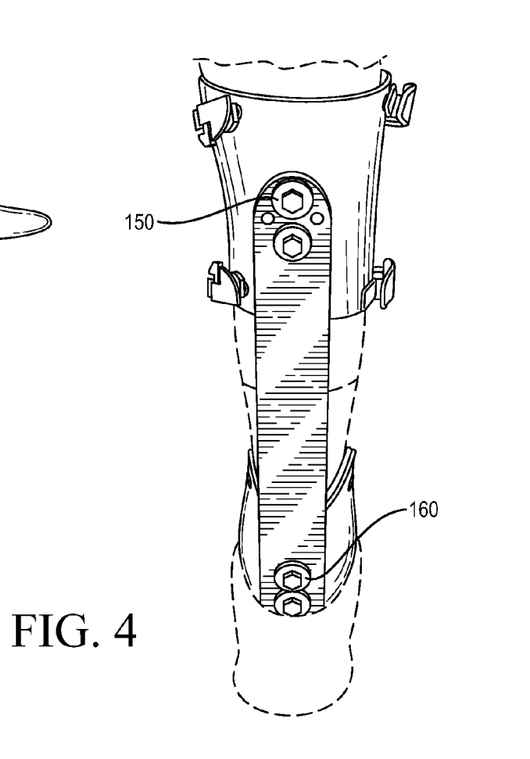
FIG. 4 is a rear view of a dynamic exoskeletal orthosis showing a posterior strut according to an embodiment of the present invention.

The exoskeletal orthosis 100 may comprise at least one mounting plate, for example, two mounting plates: a first mounting plate 150 for attaching one end of the at least one posterior strut 130 to the proximal cuff and a second mounting plate 160 for attaching an opposite end of the at least one posterior strut 130 to the ankle section/footplate 140 (as shown in FIGS. 1 and 4). In one or more embodiments, the at least one mounting plate comprises an ÖSSUR® posterior mounting plate (designed for transtibial prostheses).

The mounting plates 150, 160 may include a fastener including, but not limited to, at least one of a screw, bolt, nail, nut, adhesive, combination thereof, or any other effective fastener.

The attachment of the at least one posterior strut 130 to an ankle section/footplate 140 may be slightly more proximal than traditional orthoses. This helps offset motion within the ankle, which is often painful or severely limited in these patients, to the at least one posterior strut without compromising comfort.

D. Ankle Section/Footplate

Figures 5, 6A:
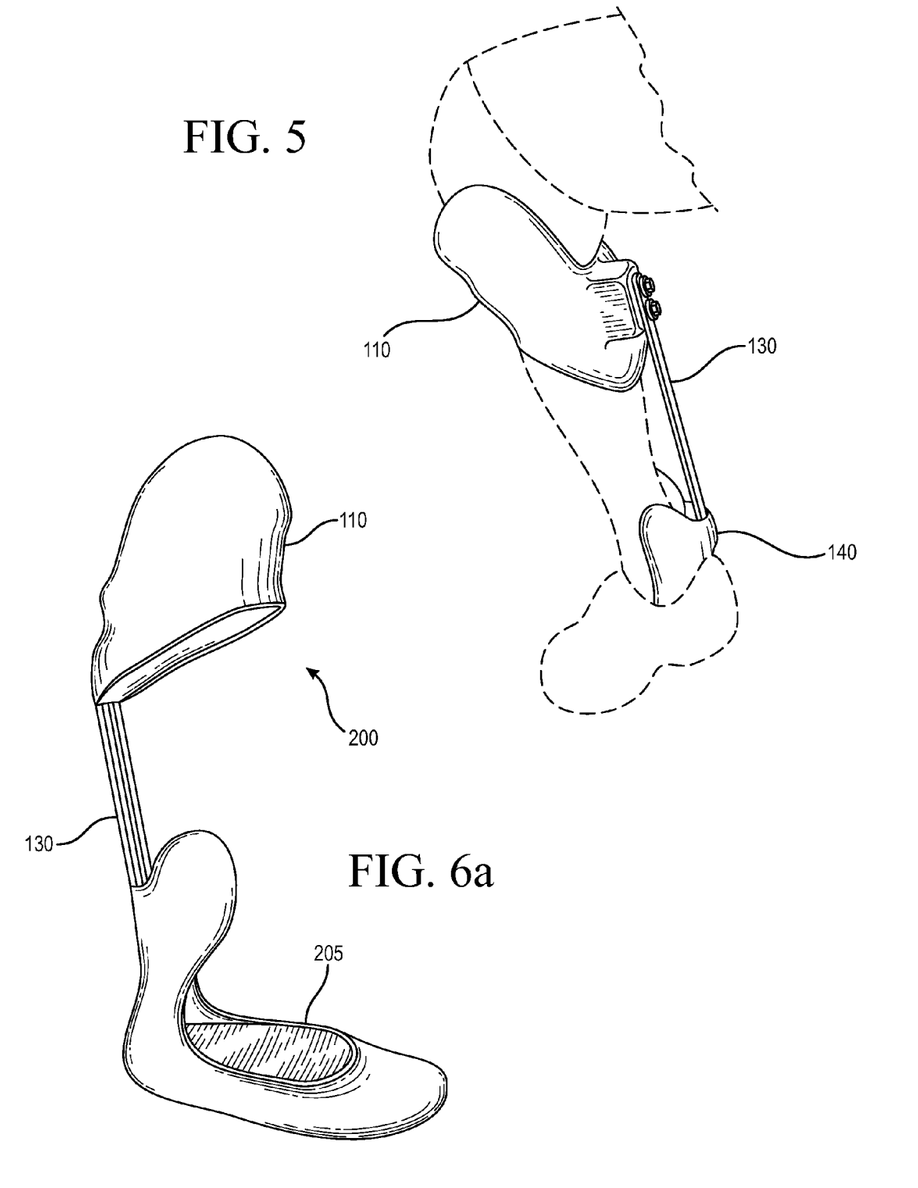
FIG. 5 is a view of a dynamic exoskeletal orthosis attached to a person's leg and foot.
FIG. 6a is a side view of a partial dynamic exoskeletal orthosis according to an embodiment of the present invention.

The exoskeletal orthosis 100 comprises an ankle section/footplate 140. The ankle section/footplate comprises a supramalleolar ankle section 170 and footplate section 180. The ankle section/footplate 140 may be a single piece comprising a reinforced carbon fiber composition. In one or more embodiments, the ankle section 170 comprises a lateral wing 190 for mediolateral stability and for fitting better in shoes or boots (FIG. 5). In one or more embodiments, the ankle section may also have a medial wing.

In one or more embodiments, the footplate section 180 has a "rollover" shape. The shape of the footplate section 180 positions an individual's toes in slight extension and extends to his or her toetips. A forefoot (end of the footplate) is set in slight plantarflexion compared to a midfoot. In one or more embodiments, the ankle section/footplate 140 may be stiff due to the layering of materials and carbon fiber. The footplate section 180 may have an arch (instead of being completely flat) and have extension at the metatarsophalangeal joints, which enables the metatarsal heads to remain in contact with the ground for a longer duration during ambulation.

The plantar surface of the footplate allows optimal function of the at least one posterior strut and long-term durability of the orthosis. As noted, the footplate section may have a gradual roller shape that begins just distal to a heel, which may have a cushion. In one or more embodiment, a portion of the heel, for example a posterior heel base, may comprise a SACH heel (solid ankle cushion heel).

During heel strike, the heel decreases impact on the limb and allows the patient to easily bring the forefoot to a floor. A cushioned heel may allow a gradually increasing load to the posterior strut as the tibia moves forward, while the plantarflexed foot position increases the degree of deflection and amount of energy storage from midstance through terminal stance. Energy storage and return is evident during agility drills, running, and sprinting activities, which are primarily performed while up on the forefoot. A distal third of the plantar surface may have a dorsiflexion radius design that maintains solid metatarsal contact to the ground for increased proprioception and control.

In a specific embodiment, the alignment of the orthosis can be adjusted on average up to about 7° of dorsiflexion, plantarflexion, and external or internal rotation and about 5° of inversion or eversion.

E. Versions of the Exoskeletal Orthosis

In a specific embodiment, the orthosis 100 may comprise cushioned foam attached to a proximal sole on a bottom portion the ankle section/footplate. The cushioned foam may be an entirely different and separate component from the orthosis, as the foam may require fabrication by a specially trained orthotist (preferably prosthetist-orthotist) and orthotic technician.

In embodiments, the orthosis may be made from modular components or fixed components. A modular version may be used during initial fittings and may be modified as patients progress during their rehabilitation, for example, progressing from a softer strut to a stiffer strut as they become stronger. The modular version may also include an external fixator (e.g., fastener and mounting plates)

In a specific embodiment, the modular version may comprise a flat bar (e.g., TRULIFE Littig) posterior strut. The posteriorly mounted 'run plate' may be utilized in a posterior-mounted running prosthesis. The alignment of the ankle section/footplate may also be modifiable. The angle of the footplate may be adjusted within 6 different planes, similar to adjustments for a prosthesis, in relation to a patient's foot and leg. In specific embodiments, the modular version may have a posterior strut that is attached to the proximal cuff proximally via an OSSUR® posterior mounted run plate with two bolts, plus a second OSSUR® posterior mounted run plate with two bolts at the distal end of the posterior strut (FIGS. 1-2).

In a specific embodiment, a fixed version may comprise a dual bar strut (e.g., MEDI CLEVER BONE™) for an overall lighter weight of the brace, use for higher loading and impact activities (greater durability), and the capacity for twisting motions of the lower leg. The fixed version allows for use inside boots and tighter clothing about the legs. The dual bar strut may be permanently attached (bonded) to the proximal cuff proximally and the foot/ankle component distally (as shown in FIG. 3). The fixed version may allow an inherent torsional component and accommodates twisting motions more than the modular version. The fixed version has subjectively shown an increased energy return and improved high intensity performance associated with its springlike effect, per verbal accounts from patients. However, it is may be possible to use a dual posterior strut configuration in a modular version.

F. Partial Foot Embodiment

Figure 6B:
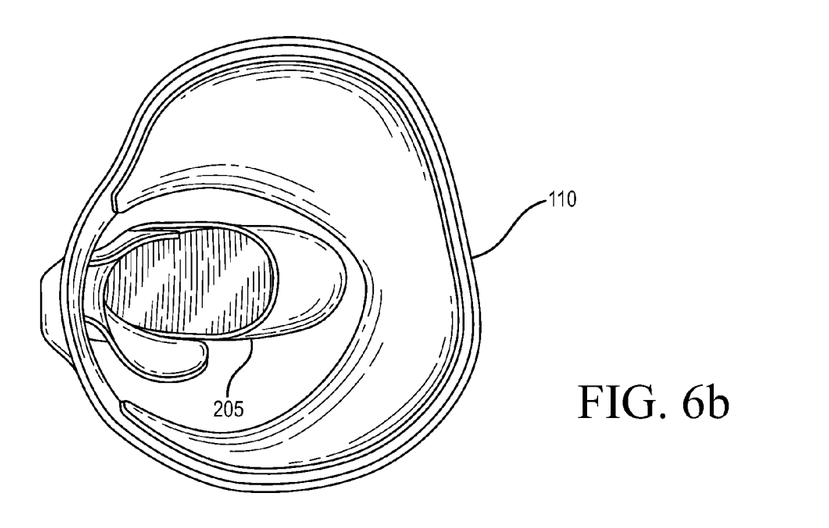

With reference now to FIGS. 6a-b, a partial foot orthosis 200 may be applied to individuals with amputation of part of the foot. The partial foot exoskeletal orthosis 200 may have a similar construction to the orthosis 100 discussed above. The partial foot orthosis 200 has a circumferential configuration of the footplate 205 (extending around the area of the foot that was amputated).

G. Other Aspects of the Exoskeletal Orthosis

Figure 7:
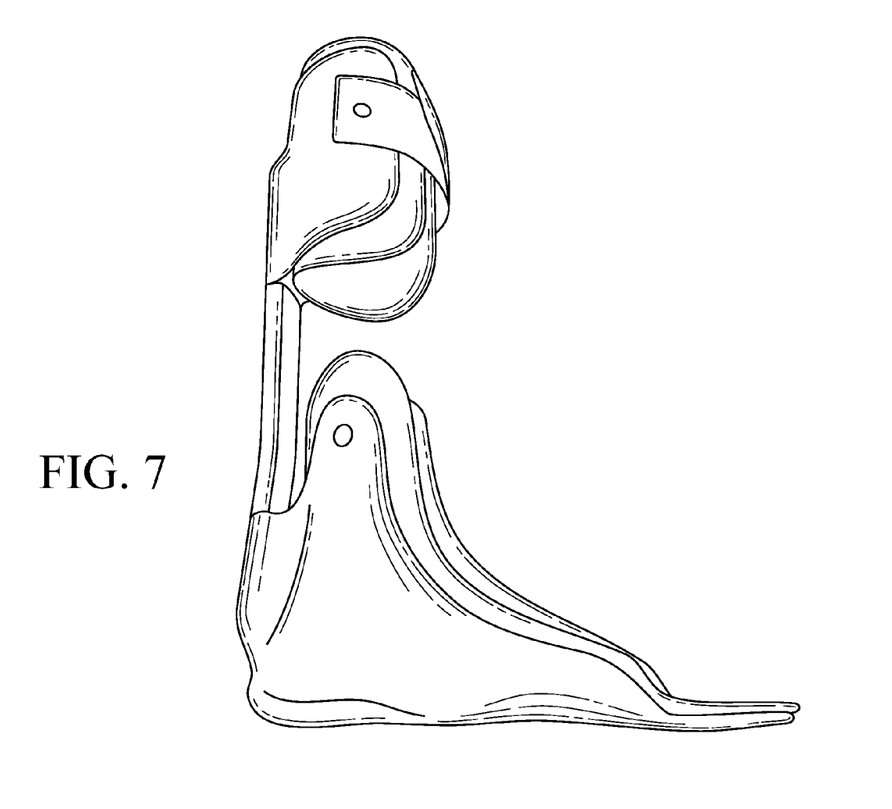
FIG. 7 is a side view of a dynamic exoskeletal orthosis according to another embodiment of the present invention.

With reference now to FIG. 7, another embodiment of the orthosis 100 is shown in which at least one of the proximal cuff 110 or ankle section/footplate 140 comprise a laminate material.

Figures 8, 9:
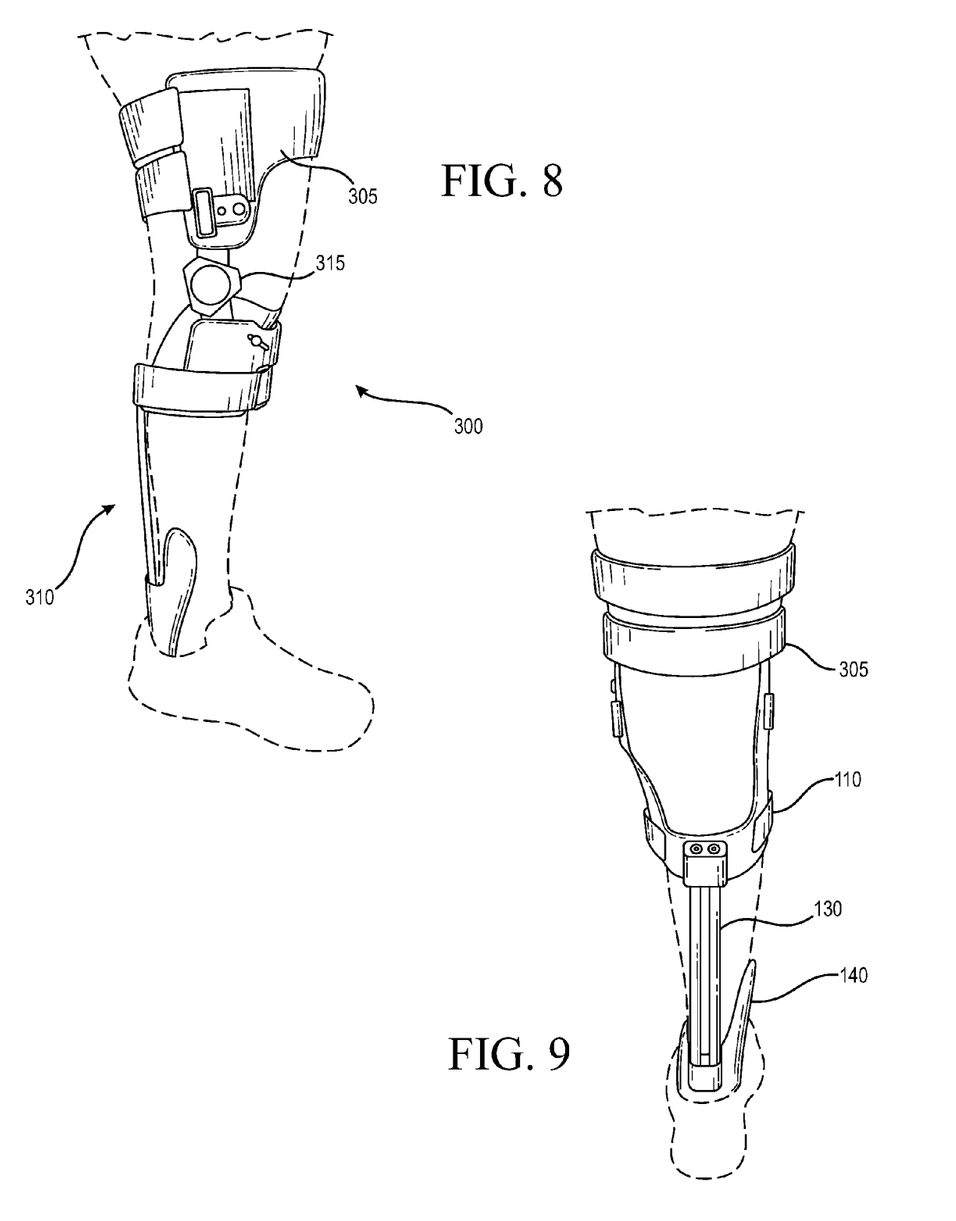
FIG. 8 is a side view of a dynamic knee ankle foot exoskeletal orthosis according to an embodiment of the present invention.
FIG. 9 is a rear view of a dynamic knee ankle foot exoskeletal orthosis according to an embodiment of the present invention.

With reference now to FIGS. 8-9, an embodiment of the present invention directed to a knee ankle foot orthosis 300 is shown. In one or more embodiments, the knee ankle foot orthosis may comprise a modular removable fabricated version that allows a patient to attach or detach a knee orthosis section 305 to a custom standard ankle foot orthosis (AFO) section 310 depending on desired activity and limb stability needs.

In one or more embodiments, the knee ankle orthosis may comprise a fixed version comprising Tm5 or original TOWNSEND knee hinges 315 with a upper anterior carbon knee orthosis cuff fused to the lower monolithic exoskeletal orthosis section. The knee ankle foot orthosis may be either modular or monolithic, and may be used for varying weaknesses, nerve injuries, ligamentous injuries, proximal knee or femoral fx's histories to allow a patient to walk, run, or perform some level of high impact activity with greater function and increased safety.

Knee ankle foot orthosis versions, both modular and monolithic, may also be used for dynamic exoskeletal orthosis cases deploying and participating in fast rope helicopter jumps, static line parachuting, or standard parachuting maneuvers to prevent potential knee injuries while using the dynamic exoskeletal orthosis for prior injury of the ankle, nerve, and the like.

The exoskeletal orthosis is a viable alternative to amputation despite severe impairment of the leg. In addition, the exoskeletal orthosis may allow at least one of: 1) a more normal walking or running pattern for those with severe injury to the leg, ankle, and/or foot that results in decreased ankle range of motion or increased pain; 2) those with an isolated peroneal neuropathy to run; 3) those with tibial neuropathy to walk and run; or 4) increased agility (stepping forward, backward, side-to-side) despite stated physical impairments. The orthosis also promotes use and subsequent strengthening of the quadriceps muscle during everyday activities. The orthosis may also be used for spinal cord injuries in which there is weakness at the ankle and at least 4 out of 5 strength in the knee.

The exoskeletal orthosis of the present invention may be modified to allow safer and more normalized gait pattern during the early postoperative period after leg/foot/ankle surgery instead of the CAM boot (a 'walking boot') The orthosis may also be used as a pediatric device for those with cerebral palsy who have ankle plantarflexion weakness associated with Achilles lengthening procedures and hamstring weakness.

Although the present invention has been described in terms of particular exemplary and alternative embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

What is claimed is:
1. An orthosis, comprising:
  a proximal cuff comprising at least one hinge along an upper edge of the cuff forming a proximal fixed axis point;
  an ankle section/footplate; and at least one posterior strut attached at a proximal end to the proximal cuff and attached at a distal end to the ankle section/footplate, thereby forming a vertical axis between the proximal cuff and the ankle section/footplate, wherein the at least one hinge allows part of a lower edge of an anterior portion of the proximal cuff to open in a direction upward and away from said vertical axis via the proximal fixed axis point while a posterior portion of the proximal cuff maintains its position.

2. The orthosis of claim 1, wherein the at least one posterior strut comprises a dual strut configuration.

3. The orthosis of claim 2, wherein each strut of the dual strut configuration has a tubular or cylindrical shape.

4. A method of treating an injury, comprising:
fitting an individual having an injury with an orthosis according to claim 1; and
placing the individual's foot with the attached orthosis inside a shoe or boot.

5. A method according to claim 4, further comprising progressing the individual from ambulation during a post-injury phase to agility and impact activities.

6. A method according to claim 4, further comprising modifying the at least one posterior strut over time, wherein a second at least one posterior strut is stiffer than a first at least one posterior strut.

7. A method according to claim 4, wherein the injury is selected from the group consisting of ankle fusion; talus or calcaneus fractures; tibial nerve injury; peroneal nerve injury; partial foot amputation; soft tissue loss in a leg; and pain in an ankle during a weight-bearing activity.

8. The orthosis of claim 1, wherein the proximal cuff comprises a reinforced carbon fiber composition.

9. The orthosis of claim 1, wherein the at least one posterior strut comprises a single strut having a rectangular bar shape.

10. The orthosis of claim 1, wherein the at least one posterior strut is integral with at least one of the proximal cuff or ankle section/footplate.

11. The orthosis of claim 1, wherein the at least one posterior strut is removably attachable to at least one of the proximal cuff or the ankle section/footplate.

12. The orthosis of claim 1, wherein the ankle section/footplate comprises a reinforced carbon fiber composition.

13. The orthosis of claim 1, wherein the at least one posterior strut has a length of about 5 inches to about 12 inches.

14. The orthosis of claim 1, further comprising a detachable knee orthosis section.

15. The orthosis of claim 1, further comprising an upper knee cuff connected to said proximal cuff via a hinge.

16. The orthosis according to claim 1, wherein the at least one hinge is configured to allow part of the lower edge of the anterior portion of the proximal cuff to open in a direction forward and away from the vertical axis, thereby providing a wider opening at a distal end than at a proximal end of the proximal cuff.

17. The orthosis according to claim 1, wherein the ankle section/footplate comprises a supramalleolar ankle section having a lateral wing.

18. The orthosis according to claim 1, wherein the ankle section/footplate comprises a footplate section extending to the tips of a user's toes and having an arch.

* * * * *